(12) United States Patent
Strobel

(10) Patent No.: US 7,754,696 B2
(45) Date of Patent: *Jul. 13, 2010

(54) APPLICATION OF WATER AND ORGANIC SOLVENT SOLUBLE IVERMECTIN FOR TOPICAL AND ORAL USE

(75) Inventor: Michael Strobel, Northfield, MN (US)

(73) Assignee: Pharmaceutical Solutions, Inc., Northfield, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/000,016

(22) Filed: Dec. 6, 2007

(65) Prior Publication Data

US 2008/0090899 A1 Apr. 17, 2008

Related U.S. Application Data

(63) Continuation of application No. 10/806,683, filed on Jun. 6, 2003, now abandoned, which is a continuation of application No. 09/910,076, filed on Jul. 23, 2001, now Pat. No. 6,627,613.

(51) Int. Cl.
*A61K 31/70* (2006.01)

(52) U.S. Cl. ........................................ 514/30

(58) Field of Classification Search ........................ None
See application file for complete search history.

(56) References Cited

U.S. PATENT DOCUMENTS

| 4,199,569 | A | 4/1980 | Chabala et al. |
|---|---|---|---|
| 4,389,397 | A | 6/1983 | Lo et al. |
| 4,440,740 | A | 4/1984 | Fix et al. |
| 5,550,153 | A | 8/1996 | Kerz |
| 5,645,856 | A | 7/1997 | Lacy et al. |
| 5,773,422 | A | 6/1998 | Komer |
| 5,788,978 | A | 8/1998 | Passeron et al. |
| 5,824,653 | A | 10/1998 | Beuvry et al. |
| 6,013,636 | A | 1/2000 | Harvey |
| 6,054,140 | A | 4/2000 | Lamberti |
| 6,063,394 | A | 5/2000 | Grosse-Bley et al. |
| 6,165,987 | A | 12/2000 | Harvey |
| 6,174,540 | B1 | 1/2001 | Williams et al. |
| 6,174,866 | B1 | 1/2001 | Smoter |
| 6,193,989 | B1 | 2/2001 | Lamberti |
| 6,214,367 | B1 | 4/2001 | Harvey |
| 6,482,425 | B1 | 11/2002 | Huet et al. |
| 6,627,613 | B2 | 9/2003 | Strobel |

FOREIGN PATENT DOCUMENTS

| EP | 0 146 414 B1 | 6/1985 |
|---|---|---|
| EP | 0 473 223 B1 | 3/1992 |
| EP | 0 537 000 A2 | 4/1993 |
| EP | 0 537 998 B1 | 4/1993 |

*Primary Examiner*—Elli Peselev
(74) *Attorney, Agent, or Firm*—Sullivan & Worcester LLP; John W. Ryan

(57) ABSTRACT

A stable, palatable solution of Ivermectin in water is provided for the mass medication of animals. The present formulation does not require the use of benzyl alcohol and is stable indefinitely in the concentrated form and for up to 30 days when mixed with water.

15 Claims, No Drawings

APPLICATION OF WATER AND ORGANIC SOLVENT SOLUBLE IVERMECTIN FOR TOPICAL AND ORAL USE

FIELD OF THE INVENTION

The present invention relates to a readily water-soluble ingestible form of Ivermectin which can be used as a palatable, stable, safe solution for mass medication of animals.

BACKGROUND OF THE INVENTION

In the mid-1970's, a survey of natural products revealed that a fermentation broth of the soil actinomycete *Streptomyces avermitilis* ameliorated infection with Nematospiroides dubius in mice. Isolation of the anthelmintic components from cultures of this organism led to discovery of the avermectins, a novel class of 16-membered lactones. Ivermectin (MECTIZAN; 22,23 dihydroavermectin Bla) is a semisynthetic analog of avermectin Bla (abamectin), an insecticide developed for crop management. More specifically, it is a mixture in the ratio of approximately 80:20 of 22,23-dihydro C-076 Bla and Blb. It is disclosed in U.S. Pat. No. 4,199,569, issued Apr. 22, 1980 to Chabala and Fisher.

Ivermectin has the following formula:

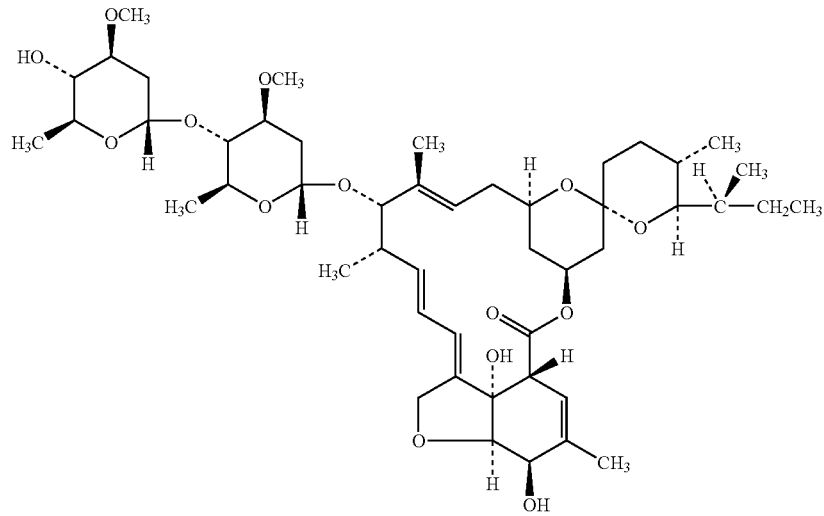

Other anthelmintic agents include; avermectin 5-oxime, abamectin, emamectin, eprinamectin, doramectin, doramectin monosaccharide 5-oximes, fulladectin, milbemycin, milbamycin 5-oxime, moxidectin, Interceptor™, nemadectin, imidacloprid, fipronil, lufenuron, thiabendazole, cambendazole, parbendazole, oxibendazole, mebendazole, flubendazole, fenbendazole, oxfendazole, albendazole, cyclobendazole, febantel, thiophanate, tetramisole-levamisole, butamisole, pyrantel, pamoate, oxantel and morantel.

Ivermectin is now used extensively to control and treat a broad spectrum of infections caused by parasitic nematodes (roundworms) and arthropods (insects, ticks, and mites) that plague livestock and domestic animals. The effects of these types of parasites can be can be serious. For example, ticks are responsible for the transmission and propagation of many human and animal diseases throughout the world. Ticks of major economic importance include Boophilus, Rhipicephalus, Ixodes, Hyalomma, Amblyomma, and Dermacentor. They are vectors of bacterial, viral, rickettsial and protozoal diseases, and cause tick paralysis and tick toxicosis. Even a single tick can cause paralysis consequent to injecting its saliva into its host in the feeding process. Tick-borne diseases are usually transmitted by multiple-host ticks. Such diseases, including Babesiosis, Anaplasmosis, Theileriosis and Heart Water are responsible for the death and/or debilitation of vast numbers of pet and food animals throughout the world. In many temperate countries, Ixodid ticks transmit the agent of a chronic, debilitating disease, Lyme disease, from wildlife to man. In addition to disease transmission, ticks are responsible for great economic losses in livestock production. Losses are attributable not only to death, but also to damage of hides, loss of growth, reduction in milk production, and reduced grade of meat.

Also, infestation of dogs and cats with fleas has several undesirable effects for the animals and their owners. Such undesirable effects include local irritation and annoying itching, leading to scratching. A high proportion of pet animals, particularly dogs, become allergic to flea saliva, resulting in the chronic condition known as flea bite allergy (or flea allergy). This condition causes the animal to bite and scratch, leading to excoriation of the skin, secondary pyogenic infection, hair loss, and chronic severe inflammatory skin changes.

Furthermore, most dogs and cats that are infested with fleas also become infected with Dipylidium caninum, the tapeworm transmitted by fleas.

In human beings, Ivermectin is the preferred drug for mass control and treatment of onchocerciasis, the filarial infection responsible for river blindness. This compound also is undergoing extensive clinical trials for use in lymphatic filariasis. Additionally, Ivermectin is effective against strongyloidiasis and several other human infections caused by intestinal nematodes.

The milbemycins are macrocyclic lactone analogues of the avermectins. Some of these compounds have antiparasitic activity similar to the avermectins and probably act by similar mechanisms.

Ivermectin is effective and highly potent against at least some developmental stages of many parasitic nematodes and insects that affect animals and human beings. The drug immobilizes affected organisms by inducing a tonic paralysis of the musculature. Early studies suggested that avermectins caused this effect primarily by modulating gamma-aminobutyric acid (GABA)-mediated neurotransmission. However, recent work indicates that paralysis of the free-living nematode *Caenorhabditis elegans* is probably mediated by potentiation, direct activation, or both, of avermectin-sensitive, glutamate-gated Cl⁻ channels. Found only in invertebrates, these channels and two of their cloned subunits have been expressed and characterized in *Xenopus lavis* oocytes. There is close correlation among activation and potentiation by avermectins and milbemycin D of glutamate-sensitive Cl⁻ current, nematicidal activity, and membrane binding affinity in this system. Glutamate-gated Cl⁻ channels probably serve as one site of Ivermectin action in insects and crustaceans as well. Avermectins also bind with high affinity to GABA-gated and other ligand-gated Cl⁻ channels in nematodes such as ascaris and in insects, but the physiological consequences are less well defined. Lack of high-affinity avermectin receptors in cestodes and trematodes may explain why these helminths are not sensitive to Ivermectin. Avermectins do interact with GABA receptors in vertebrate (mammalian) brain, but their affinity for invertebrate receptors is about 100-fold greater.

In human beings infected with *Onchocerca volvulus*, Ivermectin causes a rapid, marked decrease in microfilarial counts in the skin and ocular tissues that lasts for 6 to 12 months. The drug has little discernible effect on adult parasites, but affects developing larvae and blocks egress of microfilariae from the uterus of adult female worms. By reducing microfilariae in the skin, Ivermectin decreases transmission to the *Simulium* black fly vector. Human infections caused by gastrointestinal nematodes (e.g., strongyloidiasis, ascariasis, trichuriasis, and enterobiasis) respond well to Ivermectin; hookworms are affected to a lesser extent.

In human beings, peak levels of Ivermectin in plasma are achieved within 4 hours after oral administration. The long terminal half-life of about 27 hours in adults primarily reflects a low systemic clearance (about 1.2 liters/hour) and an apparent volume of distribution of about 47 liters. Ivermectin is about 93% bound to plasma proteins; virtually none appears in human urine in either unchanged or conjugated form. In animals, Ivermectin is recovered in feces, nearly all as unchanged drug, and the highest tissue concentrations occur in liver and fat. Extremely low levels are found in brain, even though Ivermectin would be expected to penetrate the blood-brain barrier on the basis of its lipid solubility. Recent studies in transgenic mice suggest, however, that a P-glycoprotein efflux pump in the blood-brain barrier prevents Ivermectin from entering the CNS. This and the limited affinity of Ivermectin for CNS receptors may explain the paucity of CNS side effects and the relative safety of this drug in human beings.

A single oral dose of Ivermectin (150 micro g/kg) given every 6 to 12 months is considered effective, safe, and practical for the control of onchocerciasis in adults and children 5 years or older. Most important, such therapy results in reversal of lymphadenopathy and acute inflammatory changes in ocular tissues and arrests the development of further ocular pathology due to microfilariae. Marked reduction of microfilariae in the skin and ocular tissues is noted within a few days and lasts for 6 to 12 months; the dose should then be repeated. Cure is not attained, because Ivermectin has little effect on adult *O. volvulus*. Continuing annual therapy with Ivermectin reduces transmission of *O. volvulus*, but it is not yet known how long such therapy should continue.

Initial studies indicate that single annual doses of Ivermectin (400 micro g/kg) are both effective and safe for mass chemotherapy of infections with *W. bancrofti* and *B. malayi*. Ivermectin is as effective as diethylcarbamazine for controlling lymphatic filariasis and, unlike the latter agent, can be used in regions where onchocerciasis, loiasis, or both infections are endemic.

The finding that a single dose of 150 to 200 mg of Ivermectin can cure human strongyloidiasis is encouraging, especially because this drug also is effective against coexisting ascariasis, trichuriasis, and enterobiasis. A single dose of 100 micro g/kg of Ivermectin is as effective as, and less toxic than, traditional treatment of strongyloidiasis with thiabendazole.

Ivermectin is well tolerated by uninfected human beings and other mammals. In animals, signs of CNS toxicity, including lethargy, ataxia, mydriasis, tremors, and eventually death, occur only at very high doses; dogs, particularly collie breeds, are especially vulnerable.

In human beings, Ivermectin toxicity nearly always results from Mazzotti-like reactions to dying microfilariae; the intensity and nature of these reactions relate to the microfilarial burden and the duration and type of filarial infection. After treatment of *O. volvulus* infections with Ivermectin, these side effects usually are limited to mild itching and swollen, tender lymph nodes, which arise in 5% to 35% of people, last just a few days, and are relieved by aspirin and antihistamine drugs. Rarely, more severe reactions occur that include high fever, tachycardia, hypotension, prostration, dizziness, headache, myalgia, arthralgia, diarrhea, and facial and peripheral edema; these may respond to glucocorticoid therapy. Ivermectin induces milder side effects than does diethylcarbamazine and, unlike the latter, seldom exacerbates lesions of ocular tissues in onchocerciasis. There is little evidence that Ivermectin is teratogenic or carcinogenic.

Because of its effects on GABA receptors in the CNS, Ivermectin is contraindicated in conditions associated with an impaired blood-brain barrier, e.g., African trypanosomiasis and meningitis. Caution also is advised about coadministration of Ivermectin with other agents that depress CNS activity.

A number of references teach the use of Ivermectin in a various forms. Injecting ivermectin is a highly efficient method to administer it to an animal. It is discussed in U.S. Pat. Nos. 6,214,367, 6,193,989, 6,174,540, 6,165,987, 6,054,140, 6,013,636, 5,788,978, and 5,773,422. More specifically, U.S. Pat. No. 6,214,367, U.S. Pat. No. 6,193,989, U.S. Pat. No. 6,174,540, U.S. Pat. No. 6,165,987, U.S. Pat. No. 6,054,140, U.S. Pat. No. 6,013,636 and U.S. Pat. No. 5,773,422 utilize either benzyl alcohol or oil as an injectable carrier for the ivermectin. U.S. Pat. No. 5,788,978 incorporates glycerides of caproic, caprilic and capric acids into its ivermectin formulations. Unfortunately, administering ivermectin by injection frequently causes abscesses and requires a veterinarian to administer it. As a result, animals have a high traumatization rate and resist this application, sometimes violently and dangerously.

Formulations of Ivermectin that can be administered via other delivery systems have been developed. Ivermectin can be introduced into a host transdermally. For example, U.S. Pat. No. 5,773,422 discloses a method for treating animals with a solution of N-methylpyrrolidone, 2-pyrrolidone, or mixtures of the two and ivermectin by pouring it over their skin. U.S. Pat. No. 6,013,616 also discloses a formulation of ivermectin that can be applied topically using oil as an adjuvant. However, "pour on" ivermectin compounds may cause hair and fiber loss in the animals and therefore can be undesirable.

Solid forms of Ivermectin have also been developed for use as paste or solid feed materials. U.S. Pat. No. 5,824,653 and U.S. Pat. No. 6,165,987 discuss the use of ivermectin pastes.

Ivermectin paste can be disadvantageous in that it is inefficient and causes animals to resist treatment because of its taste.

U.S. Pat. No. 6,139,989 cites several patents that disclose solid forms of Invermectin, EP 473223, EP 537000, EP 537998 and U.S. Pat. No. 4,440,740. U.S. Pat. No. 5,550,153 discusses the use of ivermectin in tablet form. A problem with tablet forms of ivermectin may concern ruminants. Ruminant animals, including cattle, sheep, giraffe, deer, goat, bison and camels, and more particularly cattle and sheep, comprise an important group of animals that require periodic administration of medicines and nutrients. Ruminants have a complex three or four compartment stomach. The rumen, the largest of the stomach compartments, serves as an important location for receiving and passing medicines and nutrients into other compartments, including the abomasum and the intestine. However, the tablet form of therapy may not lend itself to widely-practiced and acceptable therapy. That is, ruminants regurgitate what they swallow, they chew their cuds, and they may spit out conventional tablets quickly after administration. Therefore a method of administering ivermectin on a continual basis is desirable.

U.S. Pat. No. 6,174,866 discloses ivermectin incorporated into an alfalfa deriviative for use as an animal feed that could be used continuously. However, one problem with solid forms of ivermectin in general is that they are poorly absorbed by animals; therefore, it is preferred for compounds such as invermectin to be administered as solutions because they are more bio-available.

Oral liquid formulations of ivermection have been developed. U.S. Pat. No. 6,054,140 cites EP 146414 as disclosing certain non-watery liquid formulations which contain ivermectin and more precisely, those which contain ivermectin 1% in a vehicle formed by a mixture of 40% formal glycerol—60% propylene glycol.

U.S. Pat. No. 6,013,636 provides a solution suitable for oral administration containing an anthelmintic chosen from the class of macrocyclic lactones including but not limited to the avermectins, ivermectin, doramectin, abamectin, milbemycin, and moxidectin, together with a vegetable oil and a co-solvent chosen from the group comprising alcohols having 4 or more carbon atoms.

U.S. Pat. No. 5,773,422 discloses an oral solution of ivermectin. The patent uses forms of pyrrolidone as solvents because those compounds are known to have a very low order of oral toxicity (Rat LD.sub.50 4200 mg/kg).

U.S. Pat. No. 4,389,397 claims an aqueous formulation for oral administration that comprises ivermectin, a surface active agent, a co-solvent, and an additional substrate from the group of lidocaine, parabens and choline, and benzyl alcohol.

One reason for the use of non-aqueous solutions of ivermectin is identified by U.S. Pat. No. 5,773,422, namely that as a relatively insoluble compound in water, about 0.005 mg per ml at room temperature, it will preciptate. An aqueous solution is desirable so that it can be incorporated into an animals drinking supply and facilitate administration to the animal.

The art of introducing ivermectin to animals for the treatment of parasites does not currently posses a formulation (1) that is stable in water without utilizing compounds similar to benzyl alcohol, (2) that can be accepted into an animal's water supply, (4) that will not cause the animals to reject the water due to taste, (4) that is non-flammable, and (5) that can be shipped without hazardous requirements. This combination would allow a formulation to be easily administered topically or orally and to be safely transported to the site of use.

Current products on the market are given by injection or topically in organic solutions and are not compatible with water. They cannot be given orally mixed with water because the Ivermectin will precipitate out. They also typically require benzyl alcohol to retain stability. Our formulation does not require benzyl alcohol and is stable indefinitely in the concentrated form and for up to 30 days when mixed with water.

SUMMARY OF THE INVENTION

The present invention comprises a stable, palatable solution of Ivermectin in water for use in mass medicating animals. The present formulation does not require benzyl alcohol and is stable indefinitely in the concentrated form and for up to 30 days when mixed with water to produce a palatable, stable, safe solution for mass medication.

DESCRIPTION OF THE PREFERRED EMBODIMENTS

The invention consists of forming a stable solution of Ivermectin in water for use in mass medicating animals and the addition of a flavoring and sweetening agent to increase palatability.

The present invention can be used for concentrated solutions from 0.1 to 10 percent which can be diluted in both water or organic solvents such as 10 to 99 percent ethyl alcohol or isopropyl alcohol with various concentrations of water for topical use or plain tap or distilled water for oral use.

The Concentrate can be mixed via a water medicater at 1 oz. to 128 gallons of drinking water or mixed directly in a tank for direct consumption by the animals. The concentrated product is non-flammable and can be shipped without hazardous requirements unlike current topical products. This product has applications in all domestic and non domestic animals for the control of internal and external parasites without the need to handle animals individually.

The formulation consists of Ivermectin from 0.1 to 10 percent by weight mixed with a solution 50 percent propylene glycol and 50 percent Tween 80® (polysorbate 80), a sorbitan based derivative for emulsifying and dispersing substances in medicinal and food products by volume. The process consists of adding the Ivermectin to the propylene glycol and then adding the Tween 80 as a coupling agent to the mixture and stirring for 12 to 24 hours to produce the final mixture. Flavoring can be added after this and mixed for 1 hour.

A flavoring or sweetening agent may be added to increase palatability of the end solution. Any of the following agents may be used: cyclohexyl-sulfamic acid, saccharin (o-benzosulfimide), and Aspartame (i.e., L-Aspartyl-L-phenylalanine methyl ester) sold as Nutrasweet® artificial sweetener, and the like, in small amounts that are sufficient to enhance the palatability. If the animals would not be adversely affected by inclusion of sugar in the formation, then sugar can be used to sweeten the solution. In actual practice, the sweetener and the flavoring are added in amounts that overcome the taste of Ivermectin.

The following examples serve to illustrate the many applications of the present invention and should not be considered as limiting by any means.

Example 1

Ivermectin's use in the treatment of poultry: of a 10000 head flock for foul mites and round worms. 400 cc of a 5 percent concentration mixture was added to 5 gallons of water to form a stock solution that was administered over 12 hours at a dose of 180 ug per kg. This resulted in a 100 percent elimination of both the worms and mites from the birds.

Example 2

Ivermectin's use in the treatment of beef cattle: a 400 cc 5 percent solution was added to 3600 cc of a 70 percent isopropyl alcohol. The resulting mixture was then poured on the back of cattle for the treatment of Lice and Internal parasites.

Example 3

Ivermectin's use in the treatment of Swine: 400 cc of 5 percent solution was added to 10 gallons of water to form a stock solution to treat 1000-100-pound pigs in a finishing site. This is 20 mg per 100 pounds or 200 ug per pound. This resulted in a 98 percent reduction in round worms based on fecal examinations pre and post treatment.

I claim:

1. A pharmaceutical solution comprising Ivermectin, ethyl alcohol, polysorbate 80, without benzyl alcohol, N-methylpyrrolidone or 2-pyrrolodone for the treatment of a broad spectrum of infestations caused by a parasite.

2. The pharmaceutical solution of claim 1, wherein the solution is applied topically.

3. The pharmaceutical solution of claim 1, wherein the solution further comprises water or an organic solvent.

4. The pharmaceutical solution of claim 1, wherein the solution further comprises a flavoring agent.

5. The pharmaceutical solution of claim 1, wherein said solution is a water based solution.

6. The pharmaceutical solution comprising Ivermectin, isopropyl alcohol, and polysorbate 80, without benzyl alcohol, N-methylpyrrolidone or 2-pyrrolodone for the treatment of a broad spectrum of infestations caused by a parasite.

7. The pharmaceutical solution of claim 6, wherein the solution is applied topically.

8. The pharmaceutical solution of claim 6, wherein the solution further comprises water or an organic solvent.

9. The pharmaceutical solution of claim 6, wherein the solution further comprises a flavoring agent.

10. The pharmaceutical solution of claim 6, wherein said solution is a water based solution.

11. A pharmaceutical solution comprising Ivermectin, without benzyl alcohol, N-methylpyrrolidone or 2-pyrrolodone, in an amount of 0.1-10% by weight of the solution, mixed with a solution of 50% propylene glycol and 50% polysorbate 80 by volume, for the treatment of infestations caused by a parasite.

12. The pharmaceutical solution of claim 11, wherein the solution is applied topically.

13. The pharmaceutical solution of claim 11, wherein the solution further comprises water or an organic solvent.

14. The pharmaceutical solution of claim 11, wherein the solution further comprises a flavoring agent.

15. The pharmaceutical solution of claim 11, wherein said solution is a water based solution.

* * * * *